(12) United States Patent
Silman et al.

(10) Patent No.: US 9,770,365 B2
(45) Date of Patent: Sep. 26, 2017

(54) APPARATUS FOR TREATMENT OF MIDDLE EAR FLUID IN THE EARS OF INFANTS AND TODDLERS

(71) Applicants: Shlomo Silman, Brooklyn, NY (US); Michele Emmer, Brooklyn, NY (US)

(72) Inventors: Shlomo Silman, Brooklyn, NY (US); Michele Emmer, Brooklyn, NY (US)

(*) Notice: Subject to any disclaimer, the term of this patent is extended or adjusted under 35 U.S.C. 154(b) by 0 days.

(21) Appl. No.: 14/468,813

(22) Filed: Aug. 26, 2014

(65) Prior Publication Data

US 2016/0058618 A1   Mar. 3, 2016

(51) Int. Cl.
*A61F 11/00* (2006.01)
*A61M 13/00* (2006.01)
*A61M 39/24* (2006.01)

(52) U.S. Cl.
CPC .......... *A61F 11/002* (2013.01); *A61M 13/003* (2013.01); *A61M 39/24* (2013.01); *A61M 2210/0668* (2013.01)

(58) Field of Classification Search
CPC .......... A61F 11/002; A61F 2250/0082; A61M 1/0023; A61M 3/02; A61M 13/003; A61M 15/00; A61M 16/208; A61M 2210/0668; A61M 39/24; A62B 9/06
See application file for complete search history.

(56) References Cited

U.S. PATENT DOCUMENTS

| | | | | |
|---|---|---|---|---|
| 4,888,017 A | * | 12/1989 | DeVore | A61F 11/002 623/10 |
| 2005/0000520 A1 | * | 1/2005 | Silman | A61F 11/002 128/207.18 |
| 2006/0272650 A1 | * | 12/2006 | Hoogenakker | A61F 11/002 128/864 |
| 2009/0056716 A1 | * | 3/2009 | Carrier | A61M 16/1075 128/204.15 |
| 2013/0211441 A1 | * | 8/2013 | Bidarian Moniri | A61F 11/002 606/192 |

* cited by examiner

*Primary Examiner* — Bhisma Mehta
*Assistant Examiner* — Brandy S Lee
(74) *Attorney, Agent, or Firm* — Ostrolenk Faber LLP

(57) ABSTRACT

An apparatus and method is provided for reducing middle ear fluid and equalizing middle ear pressure in infants and toddlers. The apparatus coordinates the act of swallowing and the forcing of air into the nostril of the child. The coordinated actions allow air forced into the nostril to traverse the Eustachian tube when in its open state. A flexible member and a main flexible tube, connected accordingly, are both adapted to be inserted into the child's mouth and nostril, respectively, to achieve such coordination and allow air to enter the Eustachian tube when in its open state, ultimately allowing air to reach the middle ear.

5 Claims, 9 Drawing Sheets

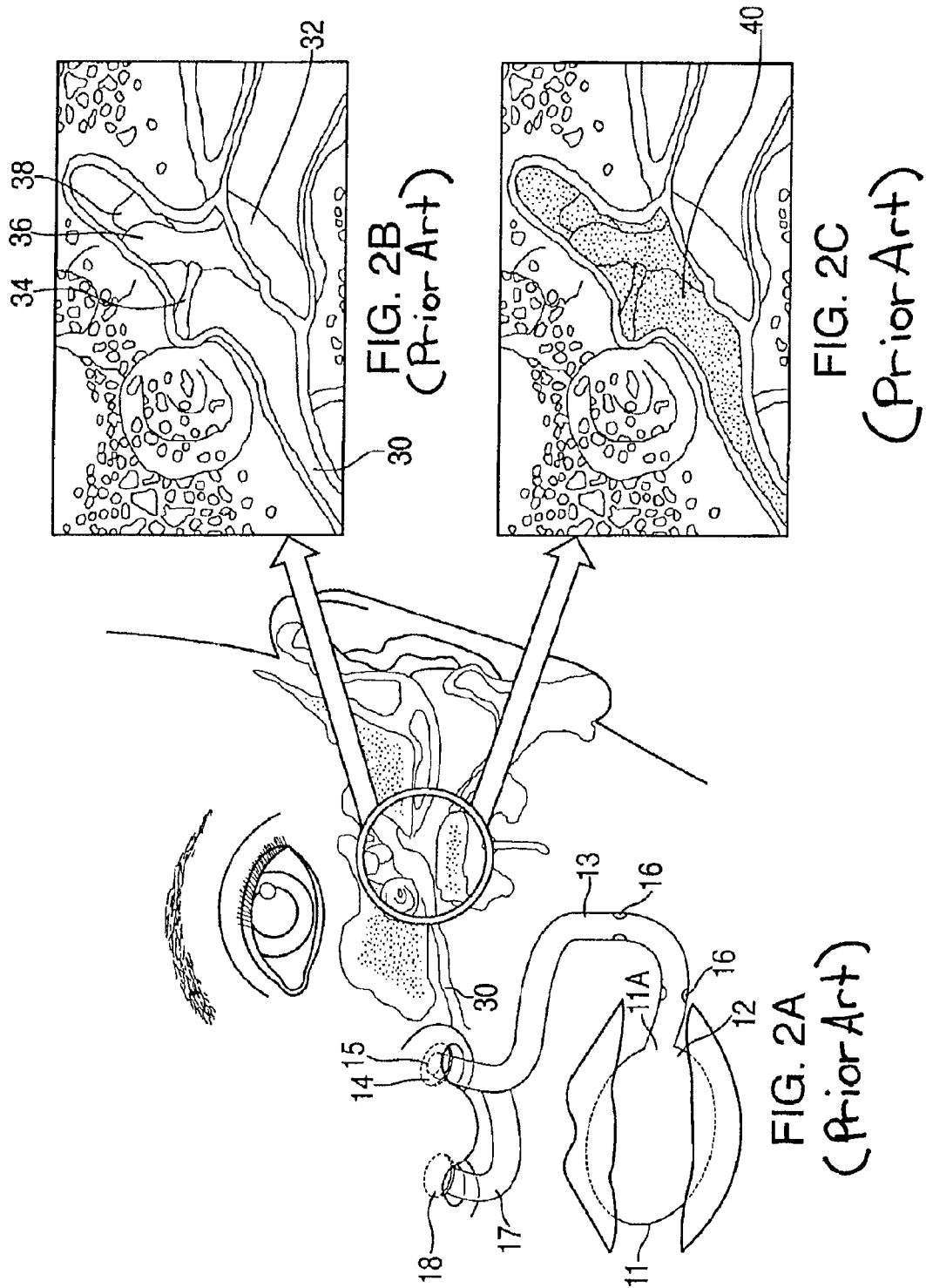

APPARATUS FOR TREATMENT OF MIDDLE EAR FLUID IN THE EARS OF INFANTS AND TODDLERS

BACKGROUND OF THE INVENTION

The present invention relates to an apparatus and method for the equalization of middle ear pressure. More specifically, the present invention relates to an apparatus and method for preventing and reducing middle ear fluid and equalizing middle ear pressure and for treatment of serous otitis media with effusion in infants and toddlers.

DESCRIPTION OF THE PRIOR ART

The Eustachian tube connects the back of the nose to the middle ear and allows air to enter the middle ear cavity behind the sealed eardrum. Contraction of the tensor veli palatini muscle is the most common way to open the Eustachian tube. This muscle contracts naturally through the act of swallowing. However, the muscle that opens the Eustachian tube in children is weaker than it is in adults. Furthermore, in an adult the Eustachian tube is rigid, approximately 3.5 to 3.9 cm in length and tilted downward by about 45 degrees. Whereas, the Eustachian tube in a child is less rigid, shorter in length and more horizontal in direction. Due to these differences between the Eustachian tubes of an adult and a child, fluid accumulated in the middle ear cavity of children is much less likely to be drained by the body though the Eustachian tube.

Serous otitis media with effusion, a common condition experienced by children, is an inflammation of the middle ear accompanied by a non-bacterial, thin, watery effusion. The main cause in children is that the Eustachian tube in children is weak and may not properly drain fluid from the middle ear. It may also be caused by inflammation of the middle ear mucosa resulting from, for example, a cold or an upper respiratory infection, blockage of or injury to the Eustachian tube, or a prior ear infection. Conservatively, 70 percent of all children will have at least one episode of middle ear effusion by the age of two. This inflammation of the middle ear mucosa may also prevent the Eustachian tube from opening normally.

When new oxygen is unable to enter the Eustachian tube, the middle ear mucosa will eventually absorb the remaining oxygen in the middle ear cavity, thus creating a vacuum and negative ear pressure, which may result in loss of hearing. Additionally, when the Eustachian tube does not open, clear fluid may eventually effuse from the mucosa of the middle ear and accumulate in the middle ear cavity, causing further hearing loss and possibly leading to further infection.

The middle ear includes the eardrum and three small bones behind the eardrum, i.e., the incus, malleus and stapes. The movement of these three bones transmits sound received by the eardrum, ultimately transmitting sound messages to the brain. Fluid in the middle ear cavity restricts movement of the eardrum and the three bones in the middle ear. Therefore, transmission of sound waves through the ear canal of children having fluid in their ears is diminished hearing.

Optimal functioning of the ear is attained when the air pressure in the middle ear cavity is equal to the ambient air pressure. When ambient air pressure is greater than or less than the air pressure in the middle ear, which may occur for example when in an airplane, pain and loss of hearing may occur. The Eustachian tube, by briefly opening, allows the body to adjust the air pressure in the middle ear so that it is equal to the ambient air pressure. This opening of the Eustachian tube is normally achieved through the act of swallowing, yawning or chewing. Eustachian tube dysfunction results when these actions do not open the Eustachian tube.

Since optimal functioning of the middle ear is attained when the air pressure in the middle ear cavity is equal to the ambient air pressure, treatment of middle ear fluid and Eustachian tube dysfunction requires a procedure for equalizing pressure and strengthening the Eustachian tube in children to accelerate the maturation of the muscle. Common treatments for serous otitis media with effusion are surgical implementation of pressure equalization tubes through the eardrum and/or the use of medication, such as steroids. The expense for such medical intervention is extremely high and makes it difficult for individuals in a lower socioeconomic position to afford such treatment. Moreover, these treatments have been shown to lack efficacy in many cases and treat merely the symptoms rather than the cause, which is the child's less effective Eustachian tube. Prevention and treatment avoiding surgery and medication are far more preferable for children, not to mention more affordable.

Current devices exist for equalizing pressure in the middle ear. For example, U.S. Pat. No. 5,885,242 describes a hand held apparatus having an air flow source for equalizing middle ear pressure. However, in order for the hand held apparatus to work, the user of the apparatus must swallow while activating the apparatus, supplying a continuous flow of air through the nostril and to the Eustachian tube. Synchronizing the acts of swallowing to open the Eustachian tube and providing a flow of air through the Eustachian tube while open is necessary to achieve equalization of middle ear pressure. Achieving synchronization of these two acts is more difficult with infants and toddlers.

A Politzer bag is routinely used in a physicians office for treating middle ear pressure and middle ear fluid. The physician places a tube in the patient's nostril and then squeezes the bag to create pressure within the nasal cavity. When the patient swallows, and pressure has built up, air will flow into the middle ear. The Politzer bag cannot, however, be used with infants and toddlers due to the high and imprecise pressure and volume flow resulting from squeezing the bag. In addition, there is again a lack of coordination between the flow of air from the bag and the act of swallowing, which need to occur almost simultaneously for the air to pass through the Eustachian tube.

In the present inventors' previously issued U.S. Pat. No. 7,285,123, an apparatus has been described that addresses the treatment of middle ear fluid in the ears of infants and which deals with the issues mentioned above. Nonetheless, the structure of the apparatus disclosed, for example, in FIG. 3 of the mentioned U.S. Pat. No. 7,285,123 patent employs valves 16*b* which, in operation, are intended to selectively close pores 16*a* to effect the functionality of the device.

In practice, it has been found that implementing the invention with the described structure is a bit more difficult, all the more so given that extra measures must be taken to prevent those valves from breaking within the tubes and possibly being forced by air into the nostrils of the child or toddler.

In view of the foregoing, an apparatus and method for the prevention and treatment of middle ear fluid and Eustachian tube dysfunction in infants and toddlers, generally ranging in age from six months to two years of age, are provided to overcome the deficiencies in the prior art.

SUMMARY OF THE INVENTION

This and other objects of the invention are accomplished in accordance with the principles of the present invention by providing an apparatus and method for preventing and reducing middle ear fluid and equalizing middle ear pressure in infants and toddlers.

An apparatus having a flexible member connected to a main flexible tube and each adapted for insertion, respectively, in the mouth and in the nostril of a nose, is provided. The flexible member defines an air chamber for holding a specified amount of air. When the flexible member is placed in a child's mouth and compressed through the act of swallowing, air in the flexible member is forced to travel through the main flexible tube and into the nostril. Pores and valves, or sealing members, may be provided along the body of the main flexible tube so as to allow for unobstructed breathing before compression of the flexible member and to close off the pores and create an air conduit between the flexible member and the nostril when the flexible member is compressed. The air forced into the nostril at the time of swallowing traverses the Eustachian tube when in its open state (resulting from the act of swallowing), ultimately allowing the air to enter the middle ear cavity.

At the time the flexible member is compressed, the opposing nostril not receiving the air forced out of the flexible member must be occluded. The opposing nostril may be occluded by a supplemental flexible tube extending from the main flexible tube or through using any other applicable method or device of occlusion (e.g., a nose plug). Pores and valves may also be provided along the body of the supplemental tube to be inserted into the opposing nostril so as to allow for unobstructed breathing before compression of the flexible member and to prevent air external to the apparatus and air forced out of the flexible member when compressed from entering the opposing nostril.

The apparatus can be employed to prevent the occurrence of middle ear fluid in children by having the infant or toddler use it for a few minutes each day as an exercise to strengthen the Eustachian tube and accelerate the maturation of the tensor veli palatini muscle.

The apparatus can also be used as necessary to treat the occurrence of middle ear fluid or to relieve an imbalance between the air pressure within the middle ear and the external air pressure.

In accordance with an embodiment of the present invention, the invention realizes an apparatus for reducing middle-ear fluid in infants and toddlers, and comprises: a flexible member, defining an air chamber and having at least one opening and configured to be compressed to force air from said chamber out through said opening and to naturally return to an original shape to create a partial vacuum in said chamber; a first nostril coupled to a first tube extending from said opening and providing an air conduit between said flexible member and said first nostril; a second nostril coupled to a second tube extending from said opening and providing an air conduit between said flexible member and said second nostril; a respective valve in each nostril that is selectively openable or closeable; an air supply tube extending for said opening in a direction away from said nostril tubes; and a one-way valve located in said air supply tube; wherein compressing said flexible member by swallowing while occluding one of said nostrils, forces air from said flexible member into said nostril which is not occluded, allowing air from said flexible member to traverse the Eustachian tube into the middle ear.

Preferably, the apparatus includes a respective valve in each nostril that is selectively openable or closeable by rotating the nostril.

Other features and advantages of the present invention will become apparent from the following description of the invention which refers to the accompanying drawings.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 2A is an illustrative view of the application of the apparatus illustrated in FIG. 1A;

FIGS. 2B and 2C are enlarged illustrative views of the middle ear section illustrated in FIG. 2A;

DETAILED DESCRIPTION OF EMBODIMENTS OF THE INVENTION

For purposes of clarity and introduction, illustrative views of the present invention are described below with initial references to prior art FIGS. 1-6. The invention concerns an apparatus and method for equalizing middle ear pressure. More specifically, the invention relates to an apparatus and method for reducing middle ear fluid and equalizing middle ear pressure and for treatment of serous otitis media with effusion in infants and toddlers.

Figure 1A:
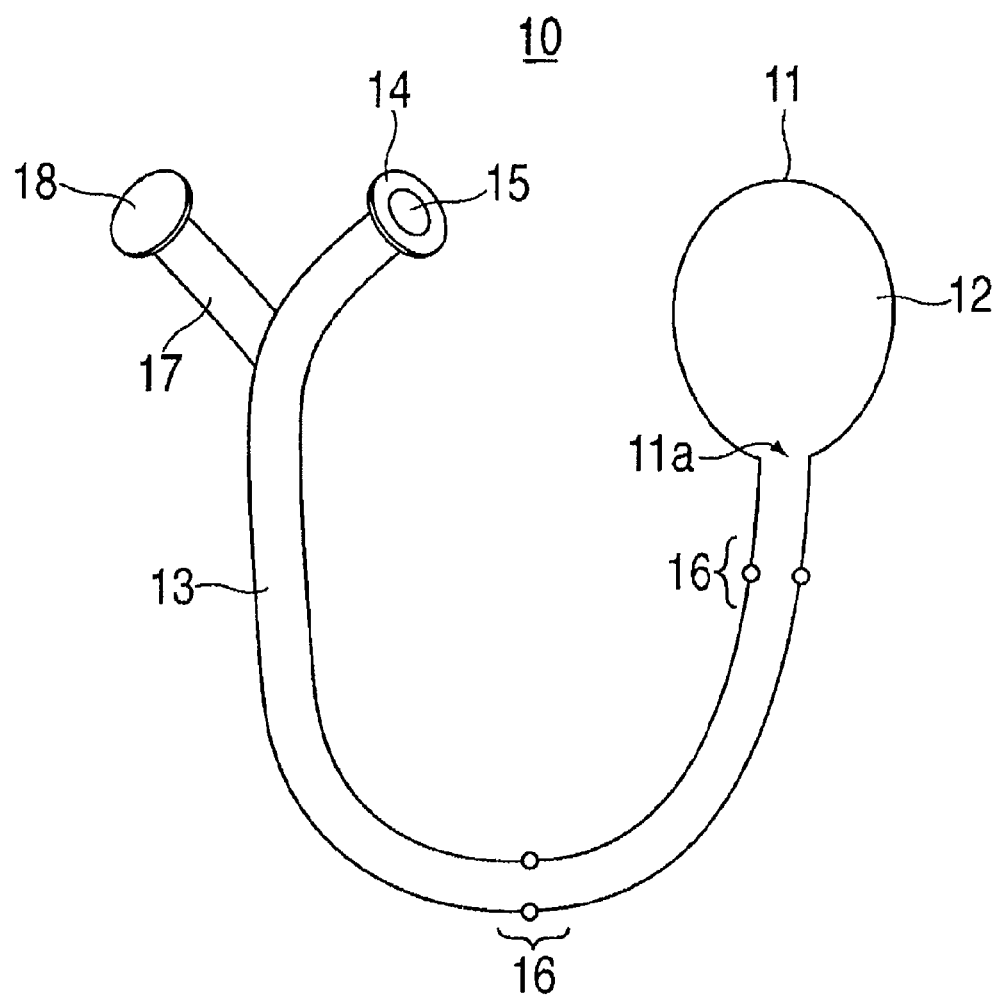
FIGS. 1A and 1B are illustrative views of an apparatus for treating middle ear fluid in accordance with the prior art.

Apparatus 10 of FIG. 1A includes a flexible member 11 defining an air chamber 12, which may have various shapes, including a bulb. A main flexible tube 13 is connected to flexible member 11 at a chamber opening 11*a* of chamber 12. Pores and valves 16 may be integrated into the body of main flexible tube 13. Main flexible tube 13 may also have a nosepiece 14 with an opening 15 to permit air flow to exit at its end. Apparatus 10 may also include a supplemental flexible tube 17 having a closed nosepiece 18 at its end.

Figure 1B:
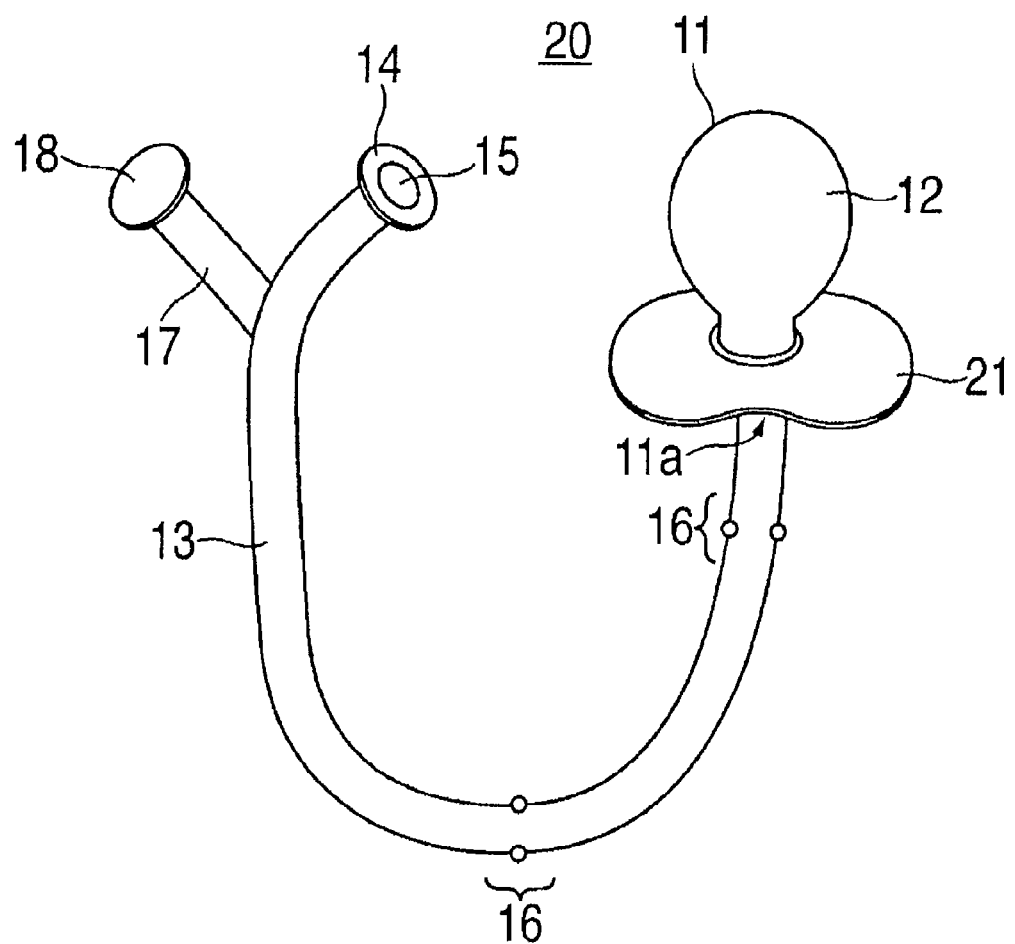

Apparatus 20 of FIG. 1B includes a mouth plate 21, which may be hard or flexible, connected to the end of flexible member 11 which may be shaped similar to a nipple, resembling an infant's pacifier. The purpose of this other preferred embodiment is to help induce an infant to receive flexible member 11 in his or her mouth. In addition, flexible member 11 may be dipped and coated with a sweet substance, such as honey, sugar water or milk, to further induce a child to accept flexible member 11 in his or her mouth.

Apparatus 20 has similar parts to apparatus 10 and is designed to operate in the same manner. Therefore the aforementioned descriptions are applicable to both embodiments. Flexible member 11 is constructed to be between 30-50 cubic centimeters in volume and is capable of providing approximately 200-600 daPa of pressure through main flexible tube 13 when flexible member 11 is compressed. Flexible member 11 is further constructed to be suitable for insertion into a mouth and is constructed with sufficient flexibility so that it may be compressed by the act of swallowing, as well as sufficient stiffness so that it is not compressed simply by insertion into the mouth. When flexible member 11 is compressed, air is forced out of chamber 12 through chamber opening 11a and forced to travel through main flexible tube 13 (described below in FIGS. 4 and 6).

Main flexible tube 13 with nosepiece 14 having an opening 15 may be adapted to be attached at the end of a first nostril. Nosepiece 14 may also be adapted for shallow insertion into the first nostril. Whether nosepiece 14 is adapted for attachment or shallow insertion into the first nostril, nosepiece 14 provides a seal from the external atmosphere. Nosepiece 14, for example, may be constructed of a soft, moldable hypoallergenic plastic that takes on the shape of the inside of a nostril to provide a seal from the external atmosphere. Alternatively, in another embodiment, main flexible tube member 13 may be adapted at one end without nosepiece 14 to be shallowly inserted in the first nostril and seal the first nostril from the external atmosphere. Upon sealing the first nostril, an air conduit is created between flexible member 11 and the nasal passageway extending from the first nostril.

Supplemental flexible tube 17 having nosepiece 18 at its end may be adapted for shallow insertion into a second nostril. When nosepiece 18 is inserted into the second nostril, the second nostril becomes sealed from the external atmosphere. Alternatively, supplemental flexible tube 17 may be adapted at one end without nosepiece 18 for shallow insertion into the second nostril to seal the second nostril from the external atmosphere. Supplemental flexible tube 17 may extend from any appropriate part of the body of main flexible tube 13. As illustrated in FIGS. 1A and 1B, supplemental flexible tube 17 is sealed off from main flexible tube 13 so as to prevent an air conduit from flexible member 11 through the body of supplemental flexible tube 17. Supplemental flexible tube 17, adapted with or without nosepiece 18, serves the purpose of occluding the second nostril, at least when flexible member 11 is compressed and air is forced through main flexible tube 13.

Apparatus 10 and apparatus 20 may also be constructed to exclude supplemental flexible tube 17. Alternatively, the second nostril may be occluded, thereby sealing the second nostril from the external atmosphere, by the use of a nose clip, a nose plug inserted into the second nostril, a finger pressed against the second nostril, or any other applicable device or method for occluding a nostril.

Apparatus 10 and apparatus 20 of FIGS. 1A and 1B, respectively, may be constructed by the combination of separate parts, such as, a flexible member part, a v-shaped flexible tube part (having main and supplemental flexible tubes), a main flexible tube absent a supplemental flexible tube part, and nosepiece parts. Apparatus 10 and apparatus 20 may also be constructed as a single unit, having proper combination of the aforementioned parts. The parts of apparatus 10 and apparatus 20 may be constructed from a soft, hypoallergenic plastic and may be disposable, either as a single unit or as individual disposable parts (e.g., nosepiece 14, flexible member 11, and/or flexible tubes 13 and 17).

FIGS. 2A-2C illustrate the application of apparatus 10 illustrated in FIG. 1A. FIGS. 2B and 2C, more specifically, provide an enlarged view, respectively, of the normal state of the middle ear and a state in which fluid has accumulated in the middle ear cavity. FIG. 2B illustrates the middle ear of a child absent middle ear fluid. The middle ear includes, as described earlier in the background of the invention, eardrum 32, the three bones, i.e., incus 38, malleus 36 and stapes 34, and Eustachian tube 30. FIG. 2C illustrates the middle ear of a child with fluid 40 in the middle ear cavity, which may significantly impact the proper functioning of incus 38, malleus 36, stapes 34 and eardrum 32 and ultimately result in hearing loss.

Apparatus 10 is used as shown in FIG. 2A to reduce middle ear fluid 40 illustrated in FIG. 2C. Apparatus 10 is made operational by inserting nosepiece 14 of main flexible tube 13 into a first nostril, occluding a second nostril (using supplemental flexible tube 17 or pressing closed the second nostril using a finger or some alternate means), inserting flexible member 11 into the mouth of the child and allowing the child to perform the act of swallowing so as to compress flexible member 11 and force pressurized air to travel through main flexible tube 13 and into the first nostril. The child can be induced to swallow by placing a few drops of milk in the child's mouth with the flexible member 11.

Apparatus 10 can be also be used as shown in FIG. 2A to prevent the occurrence of middle ear fluid 40 illustrated in FIG. 2C by strengthening the Eustachian tube and accelerating the maturation of the tensor veli palatini muscle. For this purpose, Apparatus 10 is made operational by having the infant or toddler use it for five to ten minutes, two to three times a week, even when there is no middle ear fluid 40 illustrated in FIG. 2C, employing the same method as described in FIG. 2A.

Figure 3:
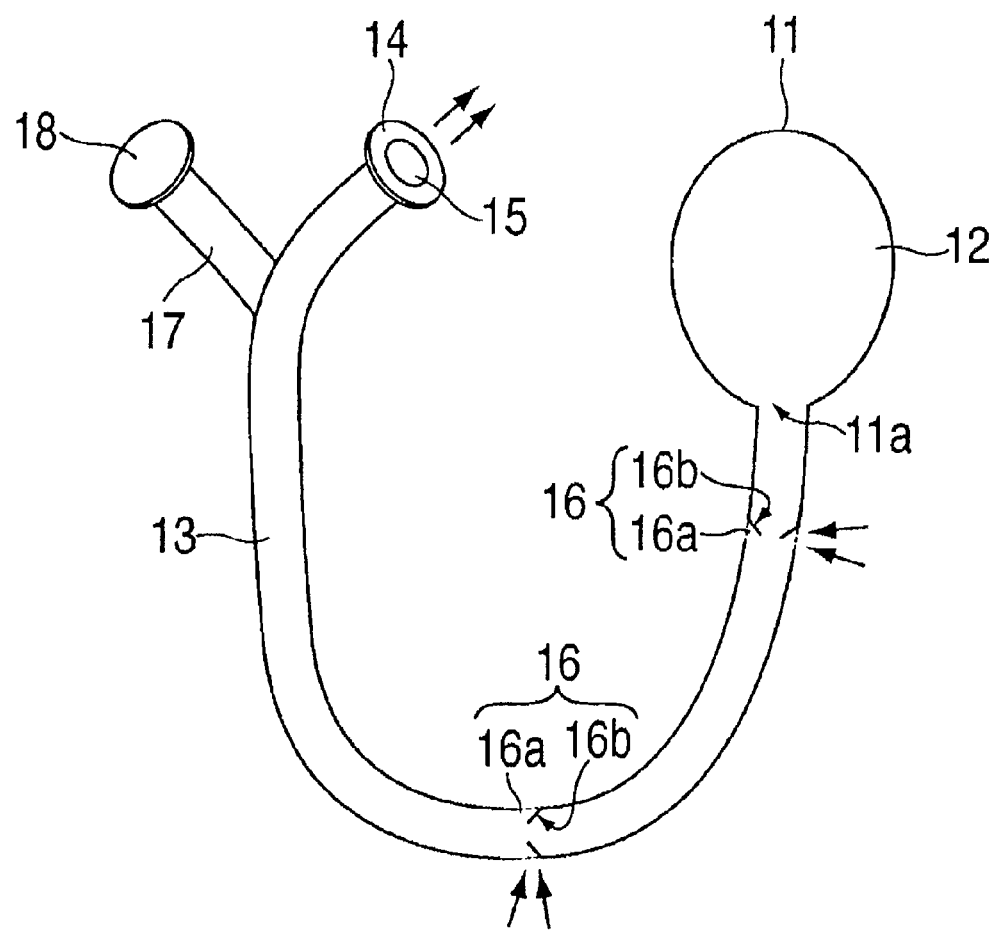
FIG. 3 is an illustrative view of the apparatus illustrated in FIG. 1A when the valves integrated along the main flexible tube are in their open position.

An enlarged view of pores and valves 16 in FIG. 1A are illustrated in FIG. 3, showing main flexible tube 13 having pores 16a and valves 16b integrated at points along the length of its body. Pores 16a are constructed so as to permit air from the outside atmosphere to flow freely in and out of main flexible tube 13. The flow of air permitted to travel through main flexible tube 13 allows for unobstructed breathing through the first nostril when main flexible tube 13 has been shallowly inserted into the first nostril. In addition, the flow of air into main flexible tube 13 allows for flexible member 11 to be inflated with air.

Figure 4:
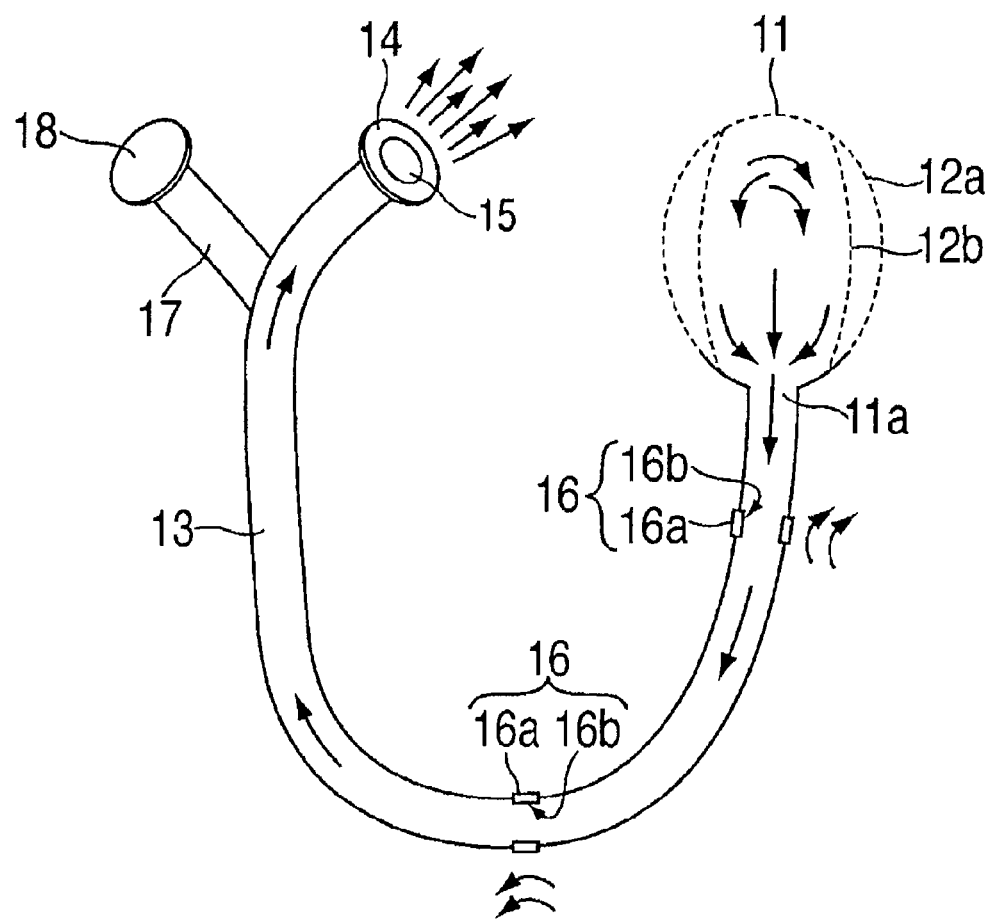
FIG. 4 is an illustrative view of the apparatus illustrated in FIG. 1A when the valves integrated along the main flexible tube are in their closed position.

Valves 16b of FIG. 3 are constructed so that when air is forced out of uncompressed air chamber 12a of FIG. 4, resulting in compressed air chamber 12b, through chamber opening 11a of flexible member 11 and into main flexible tube 13, the flow of air through main flexible tube 13 forces valves 16b, normally in an open state to allow air to flow in and out of main flexible tube 13, to close and prevent air from the outside atmosphere to enter through pores 16a, while preventing air being forced through main flexible tube 13 from exiting via pores 16a. Therefore an air conduit is formed between flexible member 11 and the nasal passageway of a nostril, as illustrated in FIG. 2A, permitting air forced through main flexible tube 13, upon swallowing and compressing flexible member 11, to enter the nasal passageway with the intended pressure. Compression of flexible member 11 forces the air contained in flexible member 11 through main flexible tube 13 and into the nasal passage of the first nostril leading to Eustachian tube 30 of FIGS. 2A and 2B. When flexible member 11 is compressed by the act of swallowing, Eustachian tube 30 is simultaneously opened by the act of swallowing, permitting air entering through the nasal passageway of the nostril to be forced through Eustachian tube 30 into the middle ear cavity. This simultaneous process equalizes middle ear pressure with that of the ambient pressure.

Figure 5:
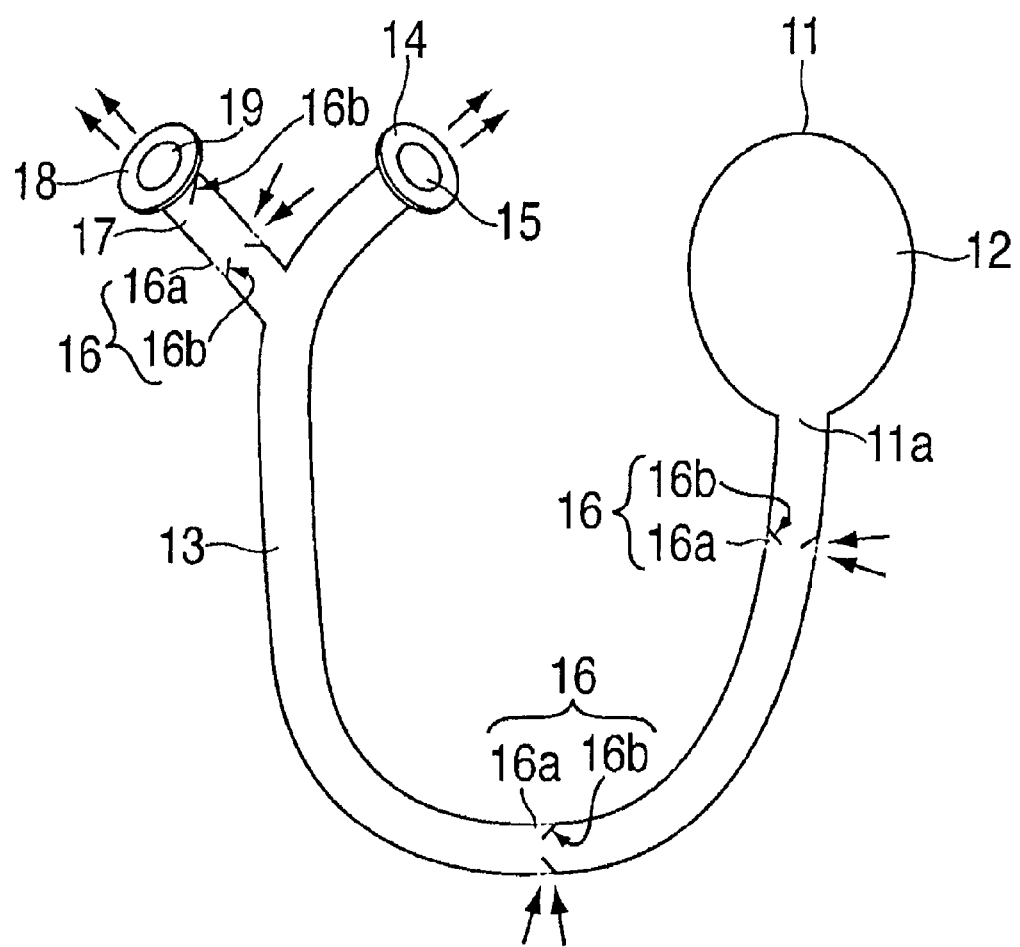
FIG. 5 is an illustrative view of an alternate embodiment of the apparatus illustrated in FIG. 1A having valves in their open position integrated along the body of the supplemental flexible tube.

An alternate embodiment of apparatus 10 of FIG. 1A is illustrated in FIG. 5. Here supplemental flexible tube 17 is constructed with pores 16*a* and valves 16*b* along its body. Supplemental flexible tube 17 is open to main flexible tube 13 or from flexible member 11. Therefore, air may enter supplemental flexible tube 17 from its pores 16*a* and from main flexible tube 13 or flexible member 11. The flow of air permitted to enter supplemental flexible tube 17 allows for unobstructed breathing through the second nostril by permitting air to flow through opening 19 of nosepiece 18 when supplemental flexible tube 17 has been shallowly inserted into the second nostril. Although supplemental flexible tube 17 ultimately serves the purpose of sealing the second nostril when air is forced into the first nostril by main flexible tube 13, unobstructed breathing is provided to both nostrils at the time main flexible tube 13 and supplemental flexible tube 17 are shallowly inserted into their respective nostrils and before flexible member 11 is compressed.

Figure 6:
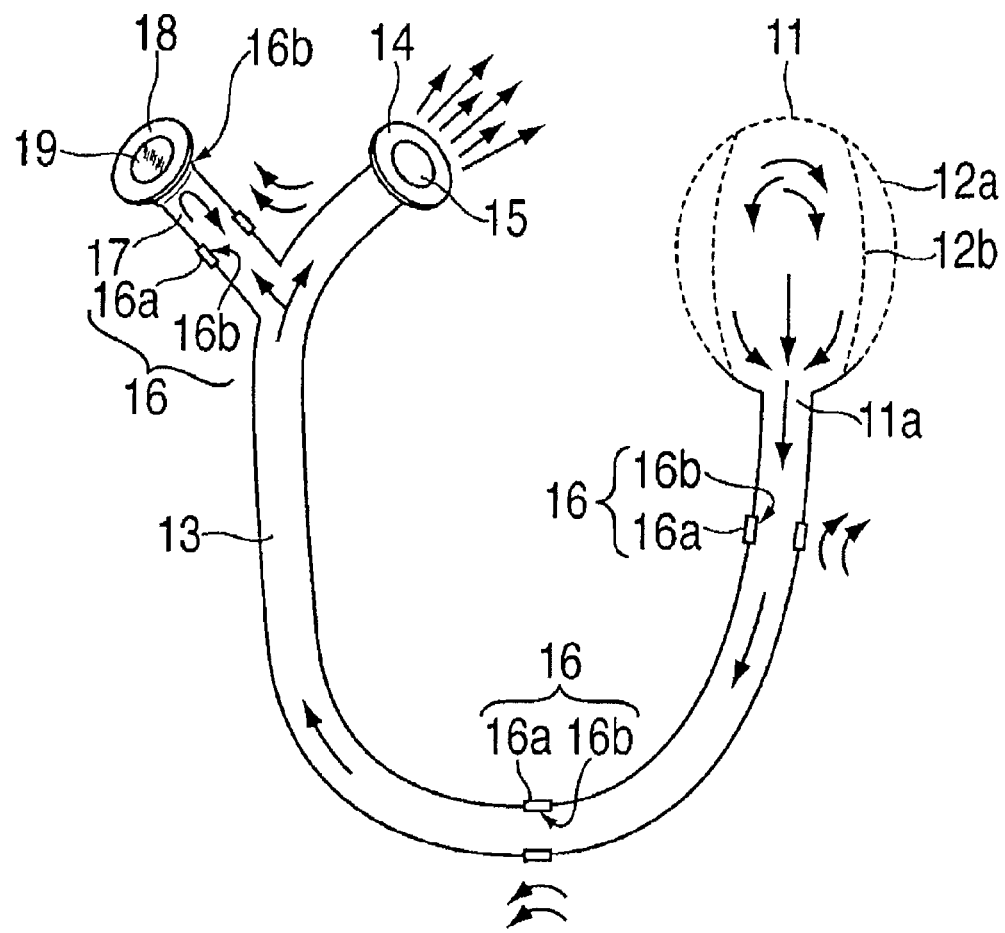
FIG. 6 is an illustrative view of an alternate embodiment of the apparatus illustrated in FIG. 1A having valves in their closed position integrated along the body of the supplemental flexible tube.

Since the second nostril must be occluded from the outside atmosphere at the time air is forced into the first nostril, valves 16*b* are also provided along the body of secondary flexible tube 17 to seal off pores 16*a* and opening 19. FIG. 6 illustrates the functionality of the alternate embodiment of apparatus 10. When air in uncompressed air chamber 12*a* of FIG. 6 is compressed by the act of swallowing, illustrated as compressed air chamber 12*b*, air is forced through chamber opening 11*a* of flexible member 11 and into main flexible tube 13 and supplemental flexible tube 17. The flow of air through main flexible tube 13 and secondary flexible tube 17 forces valves 16*b*, normally in an open state to allow air to flow freely in and out of main flexible tube 13 and secondary flexible tube 17, to close and prevent air from the outside atmosphere to enter through pores 16*a*, as well as prevent air being forced through main flexible tube 13 and secondary flexible tube 17 to exit through pores 16*a*. Therefore an air conduit is formed between flexible member 11 and the nasal passageway of the first nostril, permitting air forced through main flexible tube 13 to enter the nasal passageway of the first nostril with the intended air pressure to be forced through Eustachian tube 30 (FIG. 2A).

Figure 7:
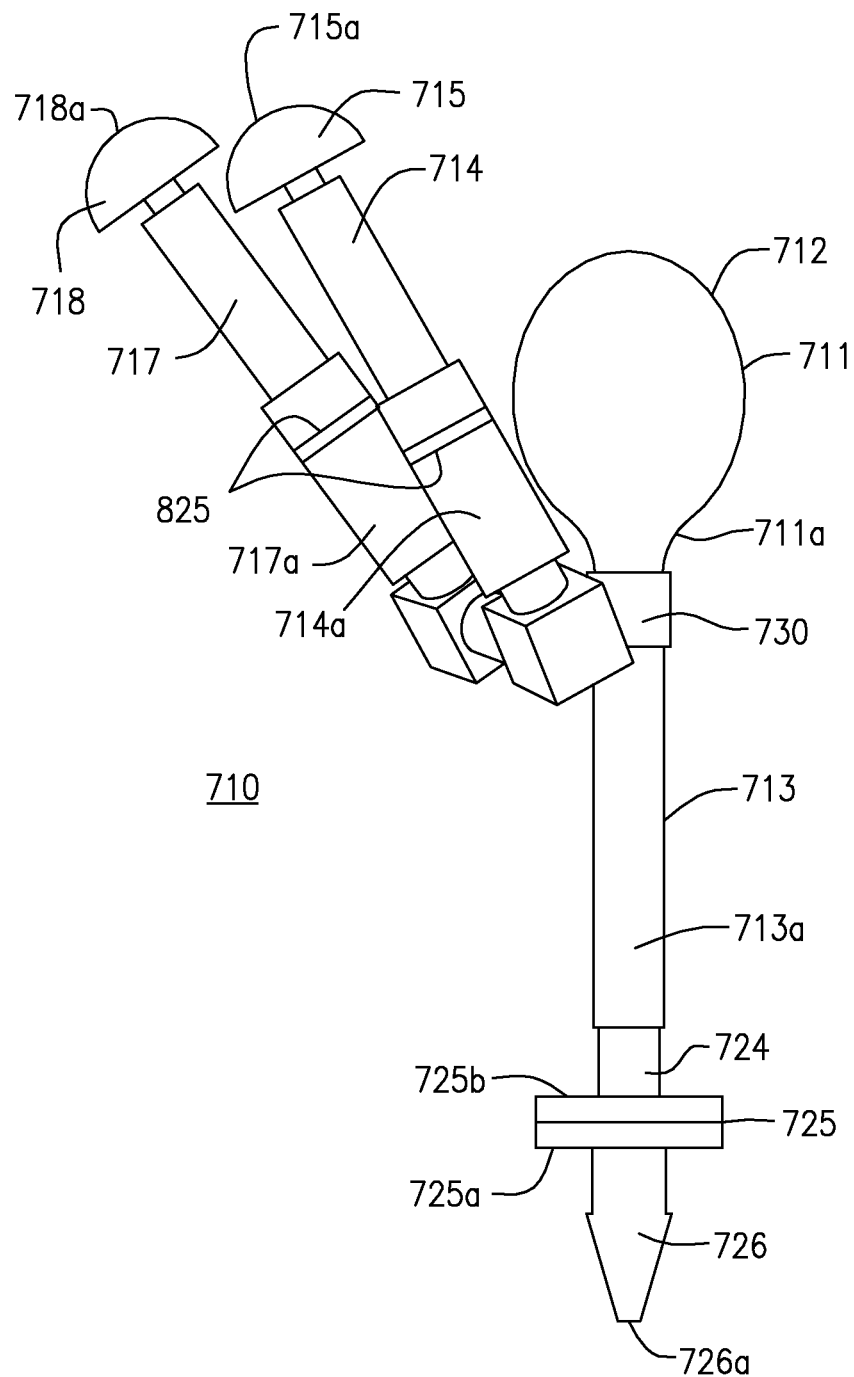
FIG. 7 perspectively depicts the improvement of the present invention over the prior art.
Figure 8A:
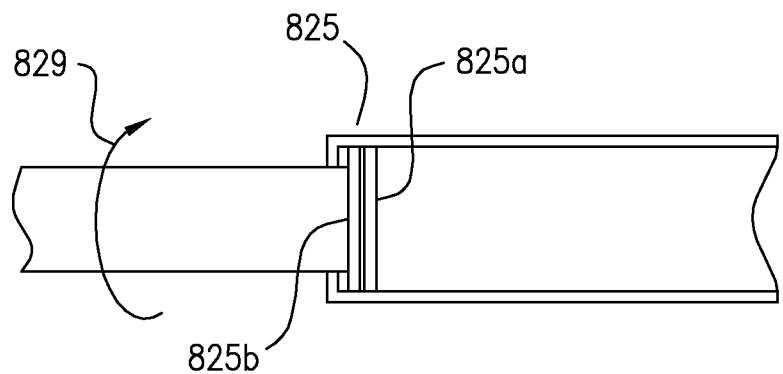
FIGS. 8*a* and 8*b* illustrate further details of the valve portion of the apparatus of FIG. 7.
Figure 8B:
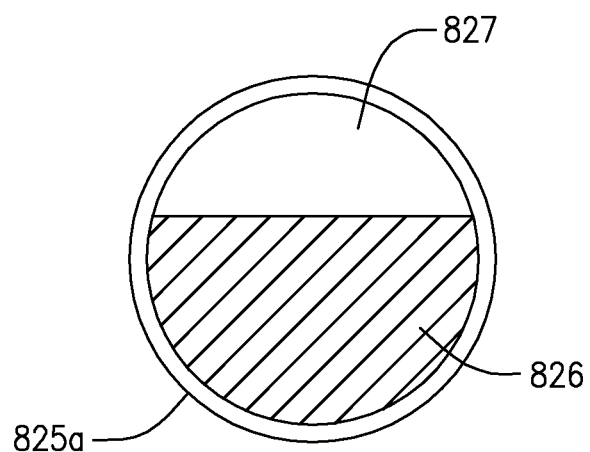

As an enhancement to the prior art, reference is made to FIGS. 7, 8*a* and 8*b*, for an improved apparatus and method for equalizing middle ear pressure in the form of a apparatus 710. The apparatus 710 of FIG. 7 includes a flexible member 711 defining an air chamber 712, which may have various shapes, including a bulb or any of the previously described shapes. An air supply tube 713 is connected to the flexible member 711 at a chamber opening 711*a* of the chamber 712.

The tube 713 has a manifold 730 to which there is respectively connected a right nose conduit 714 which terminates in a nose piece 715 and a left nose conduit 717 which terminates in a nose piece 718. Each of the nose pieces 715 and 718 has a respective nose piece opening 715*a* and 718*a*.

A one-way air valve 725 has a downstream tube 724, which is in air communication with the distal end 713*a* of the tube 713, while an opposing upstream tube 726 has a distal opening 726*a* which is exposed to the ambient air. The valve 725 has an upstream portion 725*a* and a downstream portion 725*b*.

There are different means by which one can implement a one-way valve. In the case of the valve 725, the invention preferably utilizes a pneumatic style, air-operated valve known as valve model number DCV 1604 DVN which uses as a diaphragm material a VITON one-way valve and made of a material which is plastic which has a port size of about one inch, with a 6.4 mm tubing.

Turning to the nose tubes 714 and 717, each has a respective, but otherwise identical, closeable valve 825. As illustrated in FIGS. 8*a* and 8*b*, the valve 825 can have a first disk plate 825*a* (FIG. 8*b*) which defines a circular opening which is blocked at 826 and open at 827. Adjacently and juxtaposed thereto, is another disk member 825*b* which is rotatable and has a construction essentially identical to that of the member 825*b*. Preferably, the block portion 826 is slightly larger than the corresponding opening 827. The disk components 825*a* and 825*b* are juxtaposed and rotatably slide relative to each other and are in tight contact with each other. The disk component 825 is connected to the nostril conduit 714*a*/717*a* whereby the disk component 825*b* of each nose piece are rotatable clockwise or counterclockwise, as indicated by the arrow 829.

In operation, in one rotational position of each nose piece, the blocked member 826 and the opening 827 are registered with each other, allowing air to flow from the manifold 730 to the openings in the nose pieces, whereas if one or the other of the tubes 714 and 717 are selectively turned in the opposite direction, the rotatable blocking member 826 of the disk component 825*b* blocks the corresponding opening 827, cutting off air flow completely.

In operation, a parent sets the nose pieces so that, for example, the right nose piece 714 has an unblocked air passage, while the left nose piece 718 has a closed passage. As the infant or the toddler sucks on the chamber 711, the air in the chamber 712 is forced through the manifold 730 into the right nostril, as previously described. Owing to the natural tendency of the flexible member 711 to return to its undeformed state, a positive pressure is created in the valve 725, which allows air to enter the opening 726*a* and refill the tube 713 and the flexible member 711. This operation is otherwise exactly as previously described.

Note that in the embodiment of FIGS. 7, 8*a* and 8*b*, there are no components inside the tubings to break and somehow to get introduced into the nostril of a child.

Preferably, the tube 713 is entirely flexible to allow it to be positioned in a convenient location and orientation. It might be made of a material that allows it to be bent to any desired position and to keep that position for reasons of convenience.

The nose air conduits 714 and 717 may preferably be made of a rigid or semi-rigid material so that they may be sized exactly for the spacing between the nostrils and the mouth in such a way that the blowing one's nose would not push the nose pieces 715 and 717 out of the nose. The length of each tube may be made adjustable through shallow or deeper insertion of the nose piece into the distal end of the tubing 717*a*/714*a*.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An apparatus for reducing middle-ear fluid in infants and toddlers, said apparatus comprising:
- a flexible member, defining an air chamber and having an opening and configured to be compressed to force air from said chamber out through said opening and to naturally return to an original shape to create a partial vacuum in said chamber;
- a first nose piece coupled to a first nose tube extending from said opening and providing an air conduit between said flexible member and said first nose piece;
- a second nose piece coupled to a second nose tube extending from said opening and providing an air conduit between said flexible member and said second nose piece;
- an air supply tube extending from said opening in a direction away from said first and second nose tubes; and
- a one-way valve comprising a first valve tube and a second valve tube, said first valve tube being coupled to said air supply tube and said second valve tube being coupled to ambient air; wherein compressing said flexible member by swallowing while occluding one of said nose tubes, closes said one-way valve and forces air from said flexible member into one of said nose tubes which is not occluded, allowing air from said flexible member to traverse the Eustachian tube into the middle ear, and wherein upon creation of said air partial vacuum in said chamber, said one-way valve opens and allows ambient air to enter into said air chamber.

2. The apparatus defined in claim 1, including a nose plug in said second nose tube.

3. The apparatus defined in claim 1, wherein said second nose piece is occluded by a clamp or a clip that presses against the outer edge of said second nose piece to press it closed.

4. The apparatus defined in claim 1, including a respective valve in each nose piece that is selectively openable or closeable.

5. The apparatus of claim 4, wherein each said respective valve comprises relatively rotatable disks which are controllable to either open or close said valve to airflow.

* * * * *